(12) United States Patent
DeWoolfson et al.

(10) Patent No.: US 7,402,562 B2
(45) Date of Patent: Jul. 22, 2008

(54) COMPOSITION FOR STABILIZING CORNEAL TISSUE DURING OR AFTER ORTHOKERATOLOGY LENS WEAR

(75) Inventors: Bruce H. DeWoolfson, Vienna, VA (US); Dale P. DeVore, Chelmsford, MA (US)

(73) Assignees: Euclid Systems Corporation, Herndon, VA (US); The Bruce H. DeWoolfson Irrevocable Family Trust, West Chester, PA (US)

( * ) Notice: Subject to any disclaimer, the term of this patent is extended or adjusted under 35 U.S.C. 154(b) by 31 days.

(21) Appl. No.: 11/146,153

(22) Filed: Jun. 7, 2005

(65) Prior Publication Data
US 2005/0231682 A1    Oct. 20, 2005

Related U.S. Application Data

(62) Division of application No. 10/088,032, filed as application No. PCT/US00/25190 on Mar. 14, 2002, now Pat. No. 6,946,440.

(60) Provisional application No. 60/173,801, filed on Dec. 30, 1999, provisional application No. 60/153,959, filed on Sep. 15, 1999.

(51) Int. Cl.
*A61L 12/00* (2006.01)
*A61K 38/00* (2006.01)

(52) U.S. Cl. ............... 514/2; 424/429; 530/395; 427/429

(58) Field of Classification Search ........ 514/8; 623/4.1; 512/2; 424/429; 530/395; 427/429
See application file for complete search history.

(56) References Cited

U.S. PATENT DOCUMENTS 5,270,051 A * 12/1993 Harris .................. 424/427
5,409,731 A * 4/1995 Nakagawa et al. ......... 427/2.12
5,788,957 A * 8/1998 Harris .................. 424/78.04
6,132,735 A * 10/2000 Harris et al. ............. 424/400
6,218,360 B1 * 4/2001 Cintron et al. ............ 514/8
6,537,545 B1 * 3/2003 Karageozian et al. ...... 424/94.4
2001/0016731 A1 * 8/2001 DeVore et al. ............. 606/1

OTHER PUBLICATIONS

Reddy et al. (1999) Protection against UVB inactivation (in vitro) of rat lens enzymes by natural antioxidants. Mol Cell Biochem. vol. 194, issues 1-2, pp. 41-45.*
Scott J. E. (1996) "Proteodermatan and proteokeratan sulfate (decorin, lumican/fibromodulin) proteins are horseshoe shaped. Implications for their interactions with collagen", Biochemistry, vol. 35, No. 27, pp. 8795-8799.*
Scott J. E. (1992) "Supramolecular organization of extracellular matrix glycosaminoglycans, in vitro and in the tissues", FASEB J., vol. 6, No. 9, pp. 2639-2645.*
Iozzo R. V. (1999) "The biology of the small leucine-rich proteoglycans. Functional network of interactive proteins", J. Biol. Chem., vol. 274, No. 27, pp. 18843-18846.*
Dublet et al. (1991) "Type XIV collagen, a new homotrimeric molecule extracted from fetal bovine skin and tendon, with a triple helical disulfide-bonded domain homologous to type IX and type XII collagens", J. Biol. Chem., vol. 266, No. 11, pp. 6853-6858.*
Chakravarti et al. (1998) Lumican regulates collagen fibril assembly: skin fragility and corneal opacity in the absence of lumican, J. Cell Biol., vol. 141, No. 5, pp. 1277-1286.*
Quantock et al. (2003) Annulus of collagen fibrils in mouse cornea and structural matrix alterations in a murine-specific keratopathy, Invest. Ophthalmol. Vis. Sci., vol. 44, No. 5, pp. 1906-1911.*

* cited by examiner

*Primary Examiner*—Karen Cochrane Carlson
*Assistant Examiner*—Samuel Wei Liu
(74) *Attorney, Agent, or Firm*—Finnegan, Henderson, Farabow, Garrett & Dunner, LLP

(57) ABSTRACT

An orthokeratological procedure is provided that prevents or retards relaxation of corneal tissue back to the original anterior curvature of the cornea. The procedure comprises applying a stabilizing agent that comprises fibril associated collagens with interrupted triple helices (FACITs) and/or small leucine-rich repeat proteoglycans (SLRPs) to the stabilize corneal tissue in a preselected shape.

4 Claims, 3 Drawing Sheets

FIG. 1
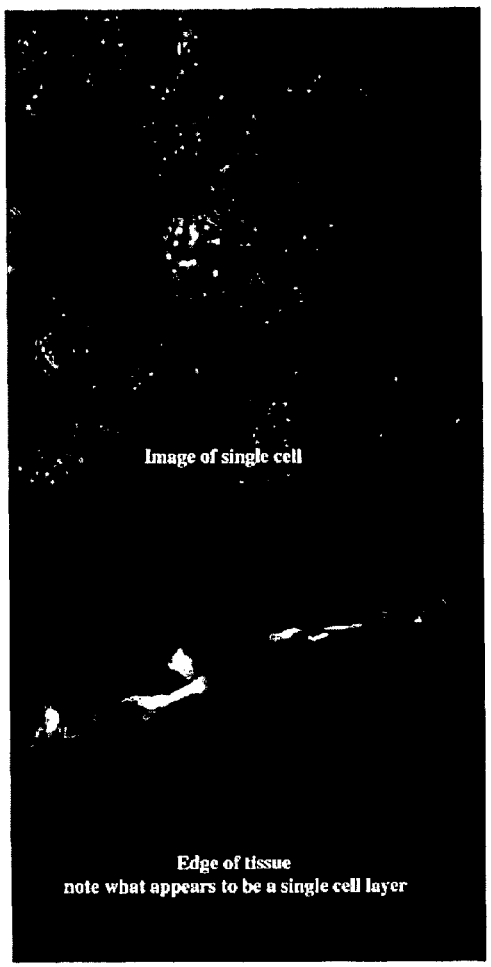
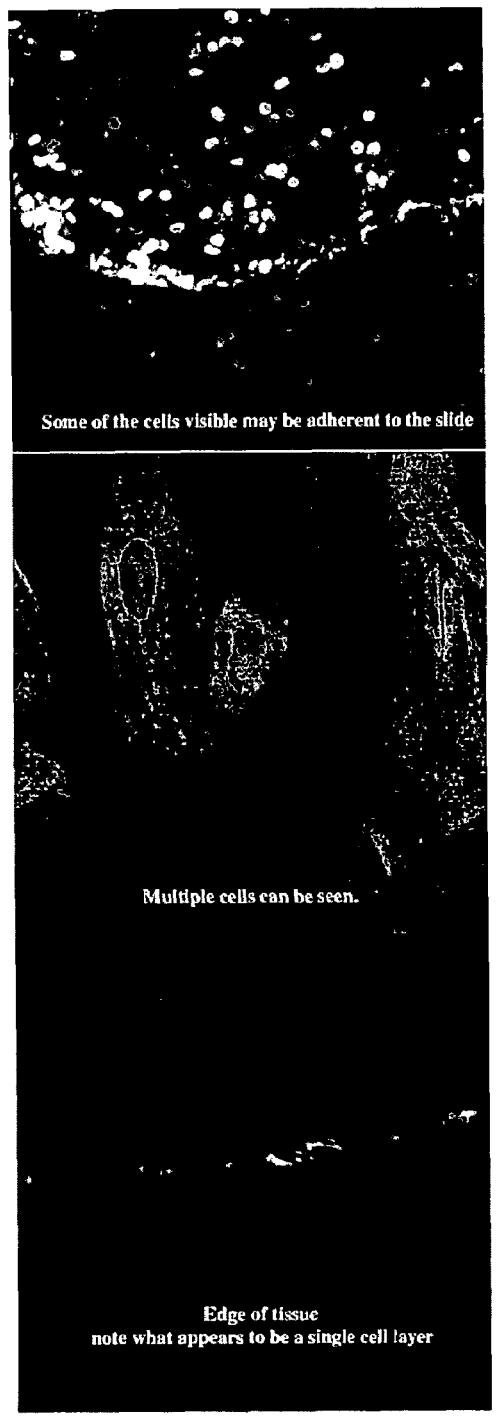

FIG. 2  SPECIMEN # 3380543

COMPOSITION FOR STABILIZING CORNEAL TISSUE DURING OR AFTER ORTHOKERATOLOGY LENS WEAR

This application is a divisional of application Ser. No. 10/088,032, now U.S. Pat. No. 6,946,440, which is the National Stage of International Application No. PCT/US00/25190, filed Sep. 15, 2000, which claims the benefit of U.S. Provisional Application No. 60/153,959, filed Sep. 15, 1999, and U.S. Provisional Application No. 60/173,801, filed Dec. 30,1999, all of which are incorporated by reference.

BACKGROUND OF THE INVENTION

1. The Field of the Invention

This invention relates to chemical compositions suitable for maintaining corneal curvature resulting from an orthokeratology procedure, and methods for making and applying the chemical compositions to a cornea for retaining the corneal curvature after undergoing orthokeratological therapy.

2. Description of the Related Art

Structure and composition of a human cornea: The cornea is the first and most powerful refracting surface of the optical system of the eye. Production of a sharp image at the retinal receptors requires that the cornea be transparent and of appropriate refractive power. The refractive power of the cornea depends primarily on two factors: its curvature and its refractive index. When the cornea is misshapened or the axial length of the eye is too long or short, or the lens of the eye is functioning abnormally, various vision related problems, such as myopia, astigmatism, hyperopia, or the like, can result. Eyeglasses or contact lenses are necessary to correct the problems. Eyeglasses correct the refractive errors by refracting the light with a lens before it reaches the cornea and to change the angle at which light enters the cornea. Contact lenses correct refractive errors of the eye by replacing the misshapened cornea with a front curve of a contact lens which is calculated to render the eye emmetropic. When the lens is taken off, however, the cornea is still misshapened or defective and refractive errors still remain.

The cornea contains 75% to 80% water on a wet weight basis. Of the remaining 20% to 25% solids, most are collagen, or other proteins, and glycosaminoglycans. Corneal fibrils, which form the skeleton of the corneal stroma, are neatly organized and present the typical 64 to 66 nm periodicity of collagen. The physicochemical properties of corneal collagen, however, do not significantly differ from those of tendon and skin collagen. Like collagen from these other sources, corneal collagen has high nitrogen, glycine, proline, and hydroxyproline contents. In boiling water or acid, corneal collagen is converted to gelatin, and collagen can be dissolved by proteolytic enzymes such as collagenase, pepsin, or papain.

Orthokeratology procedure: Orthokeratology is a nonsurgical procedure to improve refractive errors of the eye, and is an alternative to, e.g., laser eye surgery. Specifically, orthokeratology is a therapeutic procedure to reshape the curvature of a patient's cornea. A conventional orthokeratology procedure involves the use of a series of progressive contact lenses that are intended to gradually reshape the cornea and produce a more spherical anterior curvature. The process may involve the fitting of three to six pairs of contact lenses, and it has traditionally taken approximately three to six months to achieve optical reshaping. This procedure has been proven to reduce or eliminate myopia and astigmatism, hence improving natural vision and producing emmetropia (a state where vision experiences zero refractive error, or where no correction is necessary). Recent improvement in orthokeratology lens designs make it possible to achieve emmetropia much more rapidly. In many cases, this may be accomplished with a single night's wear of a single pair of end result lenses.

A problem with orthokeratology is that reshaped corneal tissue keeps a memory of its original curvature, and tends to relax and return to the original curvature after the lenses are removed. Therefore, when an orthokeratology patient reaches maximum results, retainer contact lenses are prescribed for full-time or part-time wear to stabilize the results. The retainer contact lenses have typically been made of rigid gas permeable material. Orthokeratology patients increasingly wear retainer contact lenses during the night to obtain the desired results quickly, and enjoy almost emmetropic vision during their daytime activities. A disadvantage of such a modality is that it requires the wearing of retainer lenses every night in order to keep the cornea from regressing to its former shape.

Corneoplasty: A related procedure directed to solve this problem uses a corneal softening agent to temporarily soften the cornea so that it can be more easily reshaped to a desired configuration to produce emmetropia. The corneoplasty procedure is a three-step process performed in one visit or over a period of several weeks. The three-step process includes: first, applying the softening agent to the cornea to soften corneal tissue; second, placing a rigid contact lens over the cornea to render the eye emmetropic; and third, applying a stabilizing agent. The cornea would then reshape and conform to the desired configuration dictated by the rigid contact lens. Administration of the corneal softening agent helps correct larger refractive errors in a shorter period of time.

However, it has been found that it is difficult to accurately place the shaping contact lens with respect to the axis of vision to control the reshaping of the corneal tissue. In some unsuccessful applications, corneoplasty has induced astigmatism or double vision due to errors caused by misplacing the shaping contact lens. In addition, because all three steps are performed in one visit, the patient lacks an opportunity to react to the result of reshaped corneal tissue. The patient cannot "try and see" or change his/her mind during the process.

In light of the foregoing, there is a need for an improved method for performing an acuity correcting procedure that enables the patient to quickly reach emmetropia, while retaining the option of reverting back to his prior level of vision, e.g, to make the procedure be reversible up until the patient chooses to have the correction made permanent. Furthermore, there is a need for compositions and methods for making and applying the composition that stabilizes the cornea matrix. The compositions need to be able to stabilize the corneal curvature resulting from the orthokeratology procedure so that an orthokeratology patient can dispense with wearing rigid retainer contact lenses, dispense with applying a softening agent, and yet retain the opportunity to regress to the original corneal curvature up until the patient is convinced that they want the correction made permanent.

SUMMARY OF THE INVENTION

The advantages and purposes of the invention will be set forth in part in the description which follows, and in part will be obvious from the description, or may be learned by practice of the invention. The advantages and purposes of the invention will be realized and attained by the elements and combinations particularly pointed out in the appended claims.

To attain the advantages and in accordance with the purposes of the invention, as embodied and broadly described herein, a first aspect of the present invention is directed to methods for maintaining a desired shape of corneal tissues following an orthokeratological procedure. The method comprises the step of administering to a patient a stabilizing agent form of a collagen composition comprising at least one of fibril associated collagens with interrupted triple helices ("FACIT") and small leucine-rich repeat proteoglycans ("SLRP"). The stabilizing agent stabilizes the corneal tissues to maintain the desired shape.

A second aspect of the present invention is also directed to a method for maintaining a desired shape of corneal tissue following an orthokeratological procedure. The method comprises the step of administering to a patient a stabilizing agent from a protein-derived transglutaminase whereby the stabilizing agent stabilizes the corneal tissue to maintain the desired shape.

A third aspect of the present invention is directed to a composition comprising at least one compound chosen from FACITs and SLRPs.

A fourth aspect of the present invention is directed to a method for maintaining corneal curvature resulting from an orthokeratology procedure. The method comprises the steps of applying a composition to a cornea to stabilize the corneal curvature by reacting with collagen fibrils, the composition being applied in an absence of administration of a corneal softening agent, and building bridges connecting the collagen fibrils in the cornea to constrain movement of the collagen fibrils.

A fifth aspect of the present invention is directed to a method for making a chemical composition. The method comprises the steps of dissolving at least one compound chosen from FACITs and SLRPs in a physiologically compatible solution, and buffering the solution to a physiologically compatible pH level.

A sixth aspect of the present invention is directed to a method for making a chemical composition for the application on a reshaped cornea resulting from an orthokeratology procedure. The method comprises the steps of preparing transglutaminase in a buffer solution, mixing the solution and diluting in sterile water, and adding calcium chloride.

A seventh aspect of the present invention is directed to an orthokeratological procedure to correct a patient's corneal curvature. The procedure comprises the steps of inserting an orthokeratological lens into a patient's eye to reshape unsoftened corneal tissue of the eye in a preselected shape dictated by the orthokeratological lens, and applying a stabilizing agent to the patient's eye in order to stabilize the corneal tissue in the preselected shape.

An eighth aspect of the present invention is directed to an orthokeratological system, comprising an orthokeratological lens configured to be inserted into a patient's eye to reshape unsoftened corneal tissue into a preselected corneal shape dictated by the orthokeratological lens, and a stabilizing agent administerable into the patient's eye to stabilize the corneal tissue in the preselected shape.

It is to be understood that both the foregoing general description and the following detailed description are exemplary and explanatory only and are not restrictive of the invention as claimed. Additional advantages will be set forth in the description which follows, and in part will be understood from the description, or may be learned by practice of the invention. The advantages and purposes of the invention may be obtained by means of the combinations set forth in the attached claims.

DESCRIPTION OF THE DRAWINGS

FIG. 1 shows penetration of Oregon Green 514-labeled decorin into the corneal tissue of the eye.

DESCRIPTION OF THE PREFERRED EMBODIMENTS

Figure 2:
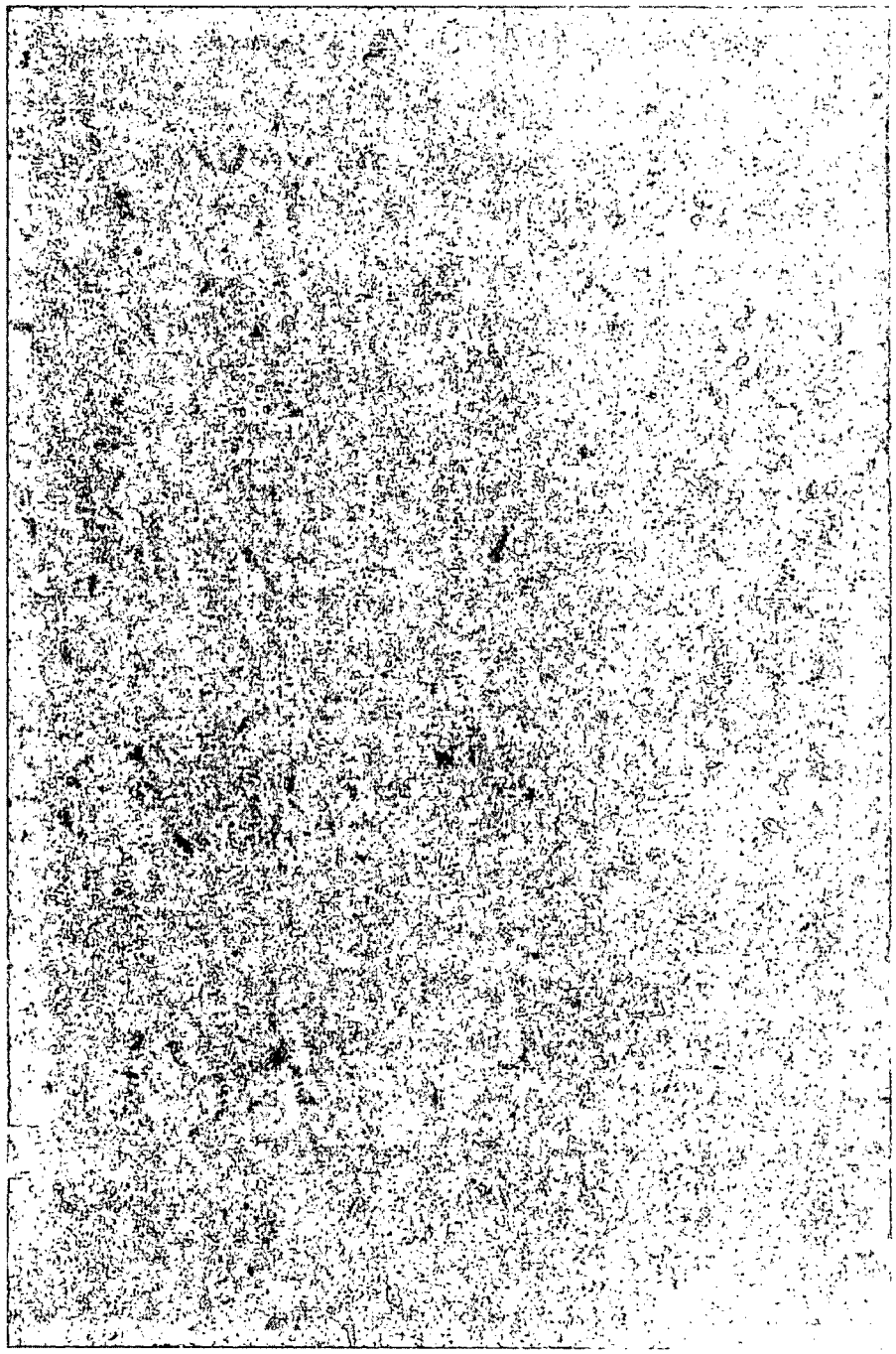
FIG. 2 shows that a cornea treated five times with decorin contains more collagen fibril-associated decorin than the untreated cornea.

Reference will now be made in detail to several embodiments of the invention. This application discloses compositions and teaches methods for making and applying such compositions to the cornea so that, when applied during or after the period of wearing the orthokeratology lens, the corneal corrective results are substantially maintained, thereby dispensing the need to wear rigid retainer contact lenses.

An accelerated orthokeratology procedure according to the present invention comprises the steps of wearing a pair of orthokeratology lenses to reshape the corneal tissues, and stabilizing the reshaped corneal tissues to retard relaxation of the cornea tissues to an original corneal curvature. The stabilizing agent renders permanent the reshaping of the corneal tissues. The accelerated orthokeratology procedure results in an emmetropic vision over a predetermined period of time, e.g., approximately 24 hours.

In the accelerated orthokeratology procedure, the patient, according to the present invention, may choose to wear the orthokeratology lenses, possibly in the evenings as retainer lenses, without applying the stabilizing agent to enjoy seeing through the reshaped corneal tissue. If the result is unsatisfactory, the patient may consult with an ophthalmologist or optometrist to examine the cornea and have a new pair of orthokeratology lenses fitted. When the patient is satisfied and decides to make this result permanent, the patient may apply the stabilizing agent to permanently stabilize the reshaped corneal tissues by retarding the relaxation of the corneal tissues to their original corneal curvature. The stabilizing agent rapidly restabilizes the corneal tissues in their new configuration after reshaping.

The orthokeratology lenses are preferably designed to gradually reshape the corneal tissue utilizing a mechanical pressure of the eyelid and a hydraulic pumping action of liquid tears, either natural or artificial.

According to the present application, at least two alternative types of compositions are disclosed which are suitable for use as a stabilizing agent. Each composition works independently and presents a different approach for stabilizing the corneal curvature. These compositions are generally characterized as a composition containing at least one FACIT or SLRP, or a transglutaminase enzyme composition.

According to a first approach of the present invention, a composition for the stabilizing agent is directed to a composition, preferably biologically compatible, suitable for stabilizing the collagen matrix of the eye. Corneal collagen fibrils are associated with natural binding macromolecleues. The stabilizing agent according to the present invention is generally composed of at least one compound selected from two such groups of macromolecules, namely fibril-associated collagens with interrupted triple helices, commonly abbreviated as "FACITs", and small leucine-rich repeat proteoglycans, abbreviated as "SLRPs."

In application, the extracellular matrix components of FACITs and SLRPs act as a stabilizing agent by cross-linking with corneal collagen fibrils and controlling the fibril diameter. The stabilizing agent may also form bridges and be involved in binding fibrils together to limit the ability of fibrils to glide past one another. These bridges allow some flexibility but limit the distance that fibrils can move.

Several types of collagens useful to form a biologically compatible collagenous reaction product of this invention can be chosen from a group including type VI collagen, type XX collagen, type XII collagen, and type XIV collagen. These types of collagens are members of the FACITs. The various types of FACITs can be extracted and purified or procured from academic sources, such as Schepens Eye Research Institute (Boston, Mass.).

The components of the stabilizing composition also include proteoglycans, such as SLRPs. Adding these SLRPs to the composition has been found to be effective in stabilizing the cornea. Despite its misleading nomenclature, SLRPs are large molecules. For example, several types of SLRPs can be chosen from decorin, keratocan, biglycan, epiphycan, lumican, mimican, and fibromodulin. Decorin includes dermatan sulfate glycosaminoglycan chains, and keratocan includes keratan sulfate glycosaminoglycan chains. Many SLRPs (such as biglycan, keratan, sulfate proteoglycan, deorin, laminin, and heparan sulfate proteoglycan) are also available from commercial sources, such as Sigma Chemical Company (Milwaukee, Wis.) ("Sigma"). Others are available from academic institutions or can be prepared by processes known in the art.

The following provides detailed descriptions of the various types of collagens in the FACIT family. Collagen proteins comprise a large, heterogeneous class of molecules that are associated with many developmental and physiological functions. At least twenty collagens have now been identified and about eleven of these are involved in the development of corneal structures. Two characteristics that all collagen molecules appear to have in common are being composed of three chains (termed α-chains) and having at least one domain in which these chains are arranged in a triple-helix. By convention, each collagen type is assigned a number (in Roman numerals), reflecting the chronological order in which it was discovered. FACITs play a major role in organizing corneal fibrillar collagens as discussed below.

It is known in the art that type VI collagen has a form of beaded filaments found in most stromal connective tissues. In the adult human corneal stroma, the molecule is present in quantities approaching that of the fibrillar collagens. These beaded filaments intertwine among, and appear to interact with the striated fibrils and corneal proteoglycans.

Studies have been done on the expression of the FACIT molecules types XII and XIV in the developing avian cornea. These studies, as detailed in "A New Fibril Associated Collagen, Type XX, Expressed in the Developing Avian Cornea," by Gordon et al. (Abstract in *"Through the Looking Glass" Macromolecular Morphogenesis* Symposium Sponsored by The Schepens Eye Research Institute, Boston, Mass., Jan. 22-23, 1999, hereinafter "Through the Looking Glass"), have identified new FACITs, including type XX, that may be involved in organizing corneal fibrils. These studies conclude that the developmental expression pattern of types XII, XIV, and XX collagen is correlated with the potential functions of these molecules in the avian cornea. The smaller amino terminal third noncollagenous (NC3) domains of type XX suggests that it may allow collagen fibrils closer proximity to each other.

It has been demonstrated in "Assembly of the Corneal Extracellular Matrix is a Multistep Process with Each Step Independently Regulated by Different Macromolecular Interactions," by David E. Birk (Abstract in "Through the Looking Glass"), that the proper development and maintenance of stromal architecture is required for corneal transparency. Fibril structure is one important determinant of corneal function. Collagen fibrils are initially assembled as intermediates, termed segments. These intermediates are incorporated into the developing extracellular matrix and as development proceeds a regulated maturation occurs. This fibril maturation involves the transformation of intermediates within the immature corneal stroma into longer, mature fibrils. In the cornea, the increase in length occurs with no change in diameter while in other tissues there is an increase in both length and diameter. The avian cornea has been used to study the regulation of collagen fibril formation. In the cornea, heterotypic interactions of collagen types I and V regulate the initial assembly of the fibril segment. Using a dominant-negative approach, the type V collagen composition determines the diameter of newly formed fibril segments. This effect is mediated by the amino terminal domain. Alterations in molecular assembly due to the presence of type V collagen limit fibril growth and favor the initiation of new fibril segments. This serves to increase the number of fibrils present during the rapid growth of the stroma.

The next step in fibril growth is an increase in length to yield the mature fibril. One study implicates the fibril-associated proteoglycans in the regulation of this step. One theory is that segments undergo a post-depositional fusion followed by molecular rearrangements that give rise to longer fibrils of the mature tissue. Based on this theory, an experiment was designed and predicted that, at different stages in development, there are temporal and spatial changes in components associated with the segment surface. These changes would serve to stabilize or destabilize the different steps in fibrillogenesis. Removing proteoglycans from the surface of isolated fibrils resulted in abnormal fibril growth, yielding longer and larger diameter fibrils. Adding back proteoglycans prevents this abnormal growth in a dose dependent manner.

In another study on the relation between "Type XII Collagen and Corneal Morphogenesis" by SundarRaj et al. (Abstract in "Through the Looking Glass"), it was determined that the developmentally regulated distribution of two alternatively spliced variants of type XII collagen might be associated with specific morphogenetic events involving tissue condensation.

The immunohistochemical analyses done by others indicated that the short valiant of type XII collagen was expressed in the rabbit corneal stroma and sclera from an early stage (day 14) of corneal development. The short form was also present in the connective tissue of the eyelids from an early stage of the eyelid fold formation. However, the long form was first expressed in the posterior stroma at a later stage (by day 24). During the later stages of pre- and postnatal development, the distribution of the long variant form progressed from the posterior to anterior stroma (a pattern similar to that of stromal condensation during corneal development). The long form was transiently expressed in subepidermal tissues in restricted regions where the eyelids had come together and fused. The appearance of type XII collagen in the corneal epithelial membrane ("BM") zone was evident just prior to the opening of the eyelids.

The study concludes that the differences in the temporal and spatial distribution of the long and the short variants of type XII collagen suggest that these variants may have different functions in corneal development. The long variant form of type XII collagen may be involved in corneal stromal condensation. Its interactions and function(s) in the BM zone are likely to be different than those in the stroma.

Therefore, the aforementioned studies related to the various types of FACITs indicate that these unique collagens interact with stromal collagen fibrils contributing to the organization of the corneal stroma to regulate fibril growth, provide corneal transparency and stability.

As previously discussed, adding SLRPs to the collagen mixture has been found to effectively stabilize the cornea. The following will discuss the SLRPs in further detail. In "Gene-Targeted Lumican-Deficient Mice: Regulation of Collagen Fibril Assembly and Corneal Transparency by Lumican," by S. Chakravarti (Abstract in "Through the Looking Glass"), a study was designed where corneal proteoglycans were hypothesized to be key regulators of a highly organized collagen matrix needed for transparency of the cornea. This study elucidated the role of lumican, a major corneal keratan sulfate ("KS") proteoglycan, in regulating collagen architecture and acquisition of corneal transparency. The study concluded that lumican played a critical role in collagen fibril assembly and corneal transparency. Progression of opacity might be a direct consequence of the age-dependent increase in collagen anomalies observed in the older mutants. A reduction in total KS content in lumican-deficient mice was likely to affect specific hydration and other physiological properties of the cornea.

In "Some Speculation on the Evolutionary Origin of the Genes for Corneal Keratan Sufate Proteoglycan Core Proteins," by G. W. Conrad et al. (Abstract in "Through the Looking Glass"), the scientists suggested that neither decorin nor lumican core protein genes were expressed in a cornea-specific manner, although lumican was glycosylated uniquely in the cornea. Mimecan was expressed in a more restricted array of tissues, whereas keratocan expression was completely, or almost completely, depending on species, cornea-specific. Sufficient genomic sequence data are now available from some vertebrates allowing comparison of the genomic structure of the mimecan gene (8 exons) with that of the keratocan gene (3 exons). Based on their nucleotide sequences, dendrograms of the family of genes expressing core proteins bearing keratan sulfate chains suggest that mimecan is distinctly more divergent in its sequence than keratocan. The primordial genome from which these genes evolved may have been simple, with introns appearing later (mimecan thus appearing late in evolution), or it may have evolved in exactly the reverse order, with primitive introns being eliminated with time (mimecan thus appearing early in evolution). Resolution of this question may derive from analysis of genomes of other organisms that have corneas.

To examine the cornea during corneal injury, a study on the relationship between "Growth Factors and Proteoglycans in the Stroma," by V. Trinkaus-Randall, et al. (Abstract in "Through the Looking Glass"), indicated that transforming growth factor β (TGFβ) played a role in the process of wound repair. TGFβ altered the composition of the extracellular matrix in stromal fibroblasts at the level of both core protein and glycosaminoglycan (GAG). The increase in perlecan might enhance the responsiveness of basic fibroblast growth factor (βFGF) and alter its binding to cell surface.

In an experiment on the "Role of Lumican in Wound Healing of Mouse Corneal Epithelium" by W. W.-Y. Kao (Abstract in "Through the Looking Glass"), it was concluded that lumican might regulate epithelial cell migration, thus contributing to cornea epithelial wound healing.

In a study relating to the "Control of Matrix Assembly and Cell Growth by Proteoglycan Signaling," by R. V. Iozzo (Abstract in "Through the Looking Glass"), it was shown that decorin, a prototype member of an expanding family of small leucine-rich proteoglycans, was directly involved in the control of matrix assembly primarily because of its ability to bind fibrillar collagen and to delay fibrillogenesis. The study also observed that decorin might act as a direct modulator of cell growth. For example, decorin levels are markedly elevated during growth arrest and quiescence, and its expression is abrogated by viral transformation. The study demonstrated that there was a direct interaction between decorin protein core and the epidermal growth factor (EGF) receptor. Therefore, the heightened biosynthesis of decorin by stromal elements in either wound healing or cancer growth might represent a natural mechanism of growth control.

Therefore, the aforementioned studies regarding SLRPs indicate that these unique matrix components bind to stromal collagen fibrils to control matrix organization and stabilize matrix composition.

According to the present invention, after the desired shape of corneal tissue has been achieved through an orthokeratological procedure, the stabilizing agent is applied to the corneal tissues to maintain the desired shape. This stabilizing agent should be applied directly to the corneal tissues. Thereafter, the shaping lens may be, but need not be, placed back into the corneal tissues until the stabilizing agent has had sufficient time to perform its function. As discussed below, it has been found that stabilizing agents of the present invention can perform their function before the cornea regresses to its former shape. However, with certain stabilizing agents, placing the orthokeratological lens back on the cornea for a day after application of the stabilizing agent may be advantageous.

FACITs and SLRPs

In a first embodiment of the present invention at least one compound chosen from FACITs and SLRPs is dissolved or suspended in a physiologically compatible buffer solution. Generally, the concentration of the FACITs will be in the range from about 10 to about 500 µg/ml. Preferably, the concentration of the FACITs will be in the range from about 20 to about 250 µg/ml, and most preferably, from about 40 to about 100 µg/ml. When SLRPs are also included either alone or in combination with the FACITs, the SLRPs have a concentration in the range, for example, from about 10 to about 500 µg/ml, from about 20 to about 25 µg/ml, from about 40 to about 100 µg/ml, and including any range of integers subsumed within these ranges.

The FACITS and/or SLRPs are diluted or dissolved in a buffer, such as a neutral pH phosphate buffer, having a concentration, for example, from about 0.005 to 0.5M at a pH ranging from 6.5 to 8.5, and preferably from about 6.8 to about 7.6. Other suitable buffers include HEPES, TRIZMA® (Sigma-Aldrich, or other supplier of TRIS buffer), or other biologically suitable buffers known in the art, which may also be in a concentration from about 0.005 to about 5M.

This stabilizing agent solution is then applied to the cornea in the form of drops for a period of time from about 1 day to about 14 days during the period of or after wearing the orthokeratology lens. The buffer system and pH may be modified to optimize interaction with corneal collagens. For example, the buffer pH may be increased to 7.6 or higher in order to open up the collagen matrix structure to increase delivery of the composition to the eye tissue. As one of skill in the art would recognize, the pH is limited by the potential for damage to the eye tissue. In general, a suitable pH would not be above 8.0 because of the danger of such damage.

This solution interacts with collagen fibrils in the cornea to control fibril diameter by forming bridges to attach one collagen fibril to another adjacent fibril. These bridges allow fibril flexibility but restrain the distance that fibrils move.

Thereafter, the corneal tissues will retain their shape without further use of reshaping lenses.

EXAMPLE 1

A series of ex vivo laboratory experiments were performed on enucleated porcine cornea to optimize the effects of stabilization. Enucleated porcine eyes were preserved in Optisol Solution and stored at 2-8° C. Treated eyes were examined visually and using biomicroscopy to monitor the effects on corneal epithelium, stroma, corneal clouding, corneal rigidity, anterior chamber response, and corneal thickness. Treated eyes underwent mechanical testing to evaluate changes in low and high modulus to evaluate the stress and strain under compressive force, as described in detail below. A decrease in low modulus indicated softening or a reduction in force needed to compress the collagenous network due to increased ability to force out fluids. In contrast, an increase in low modulus indicated stiffening. Any changes in the high modulus indicated damage to the collagen fibril network.

In the first phase of these ex vivo experiments, a total of 12 porcine eyes are prescreened. Enucleated eyes are exposed to drops of the stabilizing agent comprised of rabbit cornea type VI collagen (available from the Schlepens Eye Institute) having a concentration of 1 mg/ml and buffered with 0.005M sodium phosphate to a pH of about 7.2. The drops are applied over a 7-day period with the drops being applied twice each day after removal form Optisol and rinsing with balanced salt solution ("BSS") or phosphate buffered saline ("PBS"). Eyes are then returned to Optisol. All eyes are stored at room temperature and are exposed to natural light. Two concentrations of each agent are used for treatment. A slide is then applied to the corneal surface of the treated eyes and held in place using thumb pressure, or mechanically, generating a flattened surface. After 7 days, topographical analysis shows minimal rebound.

In the second phase of these ex vivo experiments, the same stabilizing agents are further evaluated in enucleated porcine eyes fitted with the orthokeratology lenses. The stabilizing agent is applied while wearing the orthokeratology lenses. Eyes are examined visually, by biomicroscopy, and using equipment to measure corneal curvature, such as keratometry and/or topography. The results of these experiments show minimal rebound after 7 days.

EXAMPLE 2

The test eyes received both a molding treatment with a shaping lens followed by administration of decorin, an SLRP, having a concentration of 500 µg/ml buffered with 0.04M sodium phosphate to a pH of about 7.2. The solution was applied according to the following schedule: The mold was applied on Friday afternoon, and remained there until Monday morning when the molds were removed. After the mold removal, the eyes were then exposed to 100 µl of the decorin solution. The mold was reapplied onto each eye. Then each eye was placed back into Optisol solution. The application of decorin was repeated on Tuesday and on Wednesday.

The mold was reapplied to one eye. Subjective photographic assessment of that eye showed that the treatment with decorin with the mold reapplied resulted in a flat cornea with no rebound.

With respect to the second eye, after the eye was exposed to the decorin on Wednesday, the mold was not reapplied. This was done to determine if the eye would rebound back to its original shape. After three more days, subjective photographic assessment of that eye showed that there was negligible to no rebound of the corneal tissues.

EXAMPLE 3

The test eyes received both molding treatment with shaping lens followed by administration of keratan sulfate, an SLRP, having a concentration of 100 µg/ml buffered with 0.04M disodium phosphate to a pH of about 7.2. The solution was applied according to the following schedule: The mold was applied on Friday afternoon, and remained there until Monday morning when the molds were removed. After the mold removal, the eyes were then exposed to 100 µl. The mold was reapplied onto each eye. Then each eye was placed back into Optisol solution. The application of keratan sulfate was repeated on Tuesday and on Wednesday.

The mold was reapplied to one eye. Subjective photographic assessment of that eye showed that the treatment with keratan sulfate with the mold reapplied resulted in a flat cornea with no rebound.

With respect to the second eye, after the eye was exposed to the keratan sulfate on Wednesday, the mold was not reapplied. This was done to determine if the eye would rebound back to its original shape. After three more days, subjective photographic assessment of that eye showed that there was moderate rebound of the corneal tissue.

Transglutaminase

According to a second approach to stabilizing the cornea of the present invention, the stabilizing agent, also preferably biologically compatible, may be derived from an enzyme normally found in the tissue, such as epidermis. The enzyme may include transglutaminase, for example, transglutaminase (Factor XIII) crosslinks proteins which are formed by covalent bonds between lysine and glutamine residues.

According to the present invention, transglutaminase is mixed with EDTA in a range from, for example, about 0.01M to about 0.25M or from about 0.05M to about 0.15M. The concentration of the transglutaminase. may range from about 0.01M to about 0.25M or from about 0.05M to about 0.1M, and including any range of integers subsumed within these ranges. As transglutaminase requires calcium ions to become activated, EDTA is added to the stabilizing agent solution in order to bind calcium ions that might induce premature transglutaminase activation. Of course, it will be appreciated that EDTA may not have to be added in many situations.

The solution should be buffered to a pH range from, for example, about 6.8 to 7.6, or from about 7.0 to about 7.2, or any range of integers subsumed within these ranges. Suitable buffers include glycine buffer, TRIS buffer, and Bicine buffers. However, the buffer should not contain phosphates as phosphates have a tendency to precipitate in the presence of calcium. Then, calcium chloride in a range from about 5 mM to about 50 mM, preferably from about 20 mM to about 30 mM, is added to the transglutaminase solution as a catalyst. The delivery system will comprise a two-part device to add the components during application to the cornea. Such a device will enable the user to combine the calcium catalyst with the transglutaminase solution at the appropriate time without the need for separate solutions or two separate devices.

EXAMPLE 4

The transglutaminase composition was prepared by adding 10 mg of transglutaminase to 10 mL of sterile water containing 2% sucrose, 0.1M EDTA, and 5 mM glycine buffer, pH 7.2. The transglutaminase was obtained from Sigma, Catalog No. T-5398, with a guinea pig liver or human recombinant source. The components were mixed and then diluted to 90 ml with sterile water. A second solution contained 25 mM calcium chloride.

Prior to application to the cornea, 10 mL of the calcium chloride solution was added to the transglutaminase composition and gently mixed. Droplets of this mixture were added to the surface of the cornea, just like adding eye drops, and allowed to react for about 10 minutes. The eye was then washed with sterile water or sterile buffer, e.g., "BSS," to remove excess transglutaminase mixture. As a result, the transglutaminase mixture mediated covalent crosslinks between various primary amine groups of peptide-bound lysines of collagen in the corneal stroma.

The above composition also went through a series of ex vivo laboratory experiments on enucleated porcine cornea to optimize the effects of stabilization. Enucleated porcine eyes were placed in ice until treated. Prior to treatment, each eye was placed in a bracket for stability and subjected to topographical evaluation using the Optikon 2000 system. Six topographs of each eye were taken and true composites generated. The corneal surface was dried using sterile gauze and then wetted with drops of 0.02M disodium phosphate. The wetted eyes were again dried and exposed to drops of 0.02M disodium phosphate. A glass slide was balanced on the surface of the cornea. Solutions of transglutaminase and calcium chloride ($CaCl_2$) were prepared in 50 mM TRIS buffer, pH 8.5. The pH of TRIS buffer was adjusted to 8.5 by adding 2.5N sodium hydroxide (NaOH). Transglutaminase was prepared at 1 mg/mL in 10 mL of TRIS buffer. $CaCl_2$ was prepared at a concentration of 25 mM in 50 mL of TRIS buffer.

Prior to administration, 1 mL of $CaCl_2$ solution was mixed with 9 mL of transglutaminase solution because transglutaminase requires $Ca^{++}$ as a catalyst. The transglutaminase/$CaCl_2$ solution was added dropwise to the area around the glass slide. Approximately 1 mL of enzyme solution was applied in a period of 2 minutes. The slide was then removed and the eye washed with 0.004M phosphate buffer, at pH 7.4. The eye was then reexamined topographically and photos taken. Following the topographical evaluation, the eyes were placed in Optisol for storage pending additional evaluations. Three eyes were treated using this protocol.

There were some difficulties in treating the first two eyes due to the difficulty in applying the enzyme solution while balancing the glass slide. In the third attempt, drops of transglutaminase were applied to the cornea and the slide applied to the corneal surface and held in place using thumb pressure. Drops of enzyme solution were subsequently applied to corneal surfaces around the glass slide. No flattening effect was noted in the first two eyes. The topographical results from the first eye appeared to show corneal steepening as shown in Table 1 below. However, topographical maps clearly demonstrated a flattening of the central cornea in the third eye. Refractive power was reduced by approximately 1.5 diopters. All eyes appeared clear by visual examination. Eyes were placed in Optisol for storage.

TABLE 1

Corneal Power as Measured by Topographical Mapping

| Porcine Eye No. | Pretreatment (in Diopter) | | Post-treatment (in Diopter) | |
|---|---|---|---|---|
| 1 | 38.98 | 37.33 | 42.14 | 39.2 |
| 2 | 39.89 | 37.7 | 39.98 | 37.26 |
| 3 | 40.25 | 38.16 | 38.79 | 36.83 |

After treatment, corneal buttons were dissected, placed in Optisol and shipped to Rutgers University for stress-strain analysis. In the stress-strain analysis, corneal buttons were placed on a slightly convex surface and exposed to compressive forces. Stress-strain curves represent the force per unit area of cross-section required to compress the cornea a certain amount as expressed in percentage. Resultant curves indicate several distinct phases. The lower part (low modulus region) represents the resistance to squeeze out fluid between collagen fibrils. The middle part, wherein the stress-strain curve does not change, and the upper part (high modulus region) represent compression of collagen fibrils. A reduction in low modulus indicates that the cornea is softer. An increase indicates that the corneal buttons are stiffer and have been stabilized.

Transglutaminase treatment gave encouraging results. Topographical evaluation indicated that one porcine eye treated with transglutaminase following corneal flattening using a glass slide exhibited a refractive power reduction of about 1.5 diopters after removal of the glass slide. It is important to note that two additional eyes were included in this treatment series. Glass slides were also applied to these porcine eyes. However, enzyme addition was applied with the eyes in the horizontal position and did not appear to flow under the glass slide into the cornea. In these eyes, there was no evidence of a reduction in refractive power by topographical evaluation. Since these eyes did not show flattening of the central cornea following the application of the glass slide, it was unlikely that the corneal flattening observed in the successful eye was solely a result of the application of the glass slide.

EXAMPLE 5

Additional experiments are performed to demonstrate that transglutaminase drops could effectively stabilize the cornea during orthokeratology. At least three different levels of transglutaminase are evaluated, including 10 mg/mL, 5 mg/mL, and 1 mg/mL. Three eyes per treatment are included, along with 2 sham controls, i.e., lens application with buffer drops only without transglutaminase, and one control with no treatment at all.

In this series, the experimental procedure includes placing the eyes in bracket holders, and conducting a topographical evaluation, 6 readings for each eye. Then, flattening lenses are applied and gently held in place using rubber band or other similar device. The eyes are positioned approximately 45° from horizontal, and conditioned with drops of 0.05M TRIS HCl solution, pH 7.6. While allowing the buffer to interact for a minute, transglutaminase solution is mixed with the $CaCl_2$ solution in a 9 to 1 ratio. Thereafter, the eyes are treated with calcium containing transglutaminase drops, each drop containing approximately 0.1 mL of solution, at intervals of 30 seconds for two minutes, followed by applying drops of 0.05M TRIS HCl buffer. The eyes are then topographically evaluated, examined using slit-lamp biomicroscopy, dissected from the globes, and are then shipped to Rutgers University for compression analysis.

Topographic evaluation shows a decrease of 1.5 to 2.0 in diopter power, and an increase in low modulus, showing a stiffening of the corneal tissue.

EXAMPLE 6

The test eyes received both molding treatment with shaping lens followed by administration of transglutaminase solution having a concentration of 1 mg/ml transglutaminase buffered with 0.05M TRIS HCl to a pH of about 7.2, plus calcium chloride in 0.05M TRIS HCl buffer at a concentration of 25 mM. The solution was applied according to the following schedule: The mold was applied on Friday afternoon, and remained there until Monday morning when the molds were removed. After the mold removal, the eyes were then exposed to 100 μl of the transglutaminase solution. The mold was reapplied onto each eye. Then each eye was placed back into Optisol solution. The application of transglutaminase solution was repeated on Tuesday and on Wednesday.

The mold was reapplied to one eye. Subjective photographic assessment of that eye showed that the treatment with transglutaminase with the mold reapplied resulted in a flat cornea with no rebound.

With respect to the second eye, after the eye was exposed to the transglutaminase on Wednesday, the mold was not reapplied. This was done to determine if the eye would rebound back to its original shape. After three more days, subjective photographic assessment of that eye showed that there was only slight rebound of the corneal tissues.

In summary, the present invention teaches various compositions having an eye-drop delivery system, for use during or after wearing orthokeratology lens to maintain or stabilize corneal tissue corrected by the accelerated orthokeratology procedure. The composition is applied to the cornea to bind collagen fibrils in the cornea, to control fibril diameter, and to form bridges between collagen fibrils.

The present invention anticipates that it can be used to stabilize the corneas of patients having already undergone orthokeratology. The stabilization procedure will eliminate the need to continue wearing retainer lenses to maintain the shape of the cornea. While it may be possible to simply utilize the stabilization step for these patients, it is anticipated that the cornea will have to be destabilized before it can be restabilized to take on the new configuration.

EXAMPLE 7

Protocol for Toxicity Evaluation of Decorin in the Feline Eye

The purpose of the following evaluation was to determine if (1) there is toxicity associated with the use of decorin on the eye; (2) assess the penetration of decorin into the cornea; and (3) quantitate decorin in the cornea following exogenous application of decorin.

One, three, and five daily applications of decorin were assessed using female cats (6 months to 2 years of age) with normal corneas as the model system. The decorin was obtained as a dry powder (Sigma) and reconstituted in a 0.1M phosphate buffer. In order to perform the microscopic evaluations, decorin was labeled with Oregon Green 514 using a commercially available kit from Molecular Probes.

Five cats were used in the study. Each cat was sedated prior to topical application of medication or photography of the eye. All animals received an ocular examination and photographs (whole eye, slit lamp, and endothelial cells) prior to treatment. Eyes were randomly assigned to a treatment group. The decorin was applied to the interior of a contact lens and the lens placed on the cat's eye. The lens remained on the eye for 10 minutes. All animals were observed briefly daily during the study. Three eyes were randomly assigned to a treatment or control group (1 eye). At least 2 more eyes were obtained for use as controls for each of the histograph, transmission electron microscopy (TEM), and confocal microscopy evaluations.

One eye from each of the three treatment groups was treated with Oregon Green 5149 labeled decorin.

Treatment group 1 eyes received one application of 50 ug of decorin in 100 ul buffer on day 1. Photographs and exams were obtained just after treatment and again on days 2, 4, and 8-post treatment. Exams and photos were then done weekly for the remainder of the month.

Treatment group 2 eyes received one application of 50 ug decorin in 100 ul buffer on days 1, 2, and 3. Photographs and exams were obtained just after treatment and again on days 2, 3, 5, and 8. Thereafter, exams and photos were obtained weekly for the remainder of the month.

Treatment group 3 eyes received one application of 50 ug decorin in 100 ul of buffer on days 1, 2, 3, 4, and 5. Photographs and exams were obtained daily and again on day 8. Thereafter, exams and photos were obtained weekly for the remainder of the month.

All animals were euthanized at one month. The eyes were enucleated. Each eye was cut in half. One half was fixed in formalin for histolgical analysis (H&E stain) of toxicity. The second half was further divided in half, one section was used for TEM visualization of the decorin, and the remainder was examined using confocal microscopy for those cats treated with labeled decorin.

Figure 3:
FIG. 3 shows an untreated cornea.

The results depicted in FIG. 1 (confocal micrographs) illustrate that the decorin is penetrating the corneal tissue of the eye. In addition, FIG. 2 (specimen #33080543) shows that a cornea treated five times with decorin according to the treatment protocol above (treatment group 3) contained more collagen fibril-associated decorin than the untreated cornea shown in FIG. 3 (specimen #43380562). Initial qualitative analysis indicates that the decorin filaments in the treated eye appear longer and "fatter". These "fatter" filaments were observed throughout the stormal sections, including the epithelial region, mid-stroma, and endothelial regions.

These observations indicate that exogenously added decorin can penetrate the corneal tissue of the eye and it can bind to the stromal matrix. In addition, there does not appear to be any ocular toxicity or adverse events associated with exogenous decorin application to the feline cornea.

It will be apparent to those skilled in the art that various modifications and variations can be made in the composition, the method for making the composition and method for applying such composition in the present invention, as well as other aspects of the invention without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents.

What is claimed is:

1. An orthokeratological procedure to correct a patient's corneal curvature, comprising the steps of:
   a. inserting an orthokeratological lens into a patient's eye to reshape unsoftened corneal tissue of the eye in a preselected shape dictated by the orthokeratological lens; and b. applying a stabilizing agent chosen from fibril associated collagens with interrupted triple-helixes ("FACIT") and small leucine-rich repeat proteoglycans ("SLRP") to the patient's eye in order to stabilize the corneal tissue in the preselected shape, wherein the SLRPs are chosen from bicilycan, decorin, epiphycan, keratocan, mimican, fibromodulin, and any combination thereof.

2. The procedure of claim 1, further comprising a step of removing the orthokeratological lens before applying the stabilizing agent.

3. The procedure of claim 1, further comprising the step of removing the orthokeratological lens after applying the stabilizing agent.

4. The method of claim 1, wherein the FACITs are chosen from type VI, type XII, type XIV, type XX, and any combination thereof.

* * * * *

UNITED STATES PATENT AND TRADEMARK OFFICE
CERTIFICATE OF CORRECTION

| | | |
|---|---|---|
| PATENT NO. | : 7,402,562 B2 | Page 1 of 1 |
| APPLICATION NO. | : 11/146153 | |
| DATED | : July 22, 2008 | |
| INVENTOR(S) | : DeWoolfson et al. | |

It is certified that error appears in the above-identified patent and that said Letters Patent is hereby corrected as shown below:

Claim 1, column 15, line 6, "bicilycan," should read --biglycan,--.

Signed and Sealed this

Sixteenth Day of September, 2008

JON W. DUDAS
*Director of the United States Patent and Trademark Office*